United States Patent
Pfeiffer et al.

(10) Patent No.: US 11,162,950 B2
(45) Date of Patent: Nov. 2, 2021

(54) ZONAL NANOFLUIDIC ANTI-TAMPER DEVICE FOR PRODUCT AUTHENTICATION

(71) Applicant: International Business Machines Corporation, Armonk, NY (US)

(72) Inventors: Dirk Pfeiffer, Croton-on-Hudson, NY (US); Joshua T Smith, Croton-on-Hudson, NY (US); Benjamin H Wunsch, Mount Kisco, NY (US)

(73) Assignee: International Business Machines Corporation, Armonk, NY (US)

( * ) Notice: Subject to any disclaimer, the term of this patent is extended or adjusted under 35 U.S.C. 154(b) by 223 days.

(21) Appl. No.: 16/203,657

(22) Filed: Nov. 29, 2018

(65) Prior Publication Data

US 2020/0174010 A1    Jun. 4, 2020

(51) Int. Cl.
| | |
|---|---|
| B01L 3/00 | (2006.01) |
| G01N 33/58 | (2006.01) |
| G01N 21/64 | (2006.01) |
| G01N 27/447 | (2006.01) |
| B82Y 30/00 | (2011.01) |
| B82Y 15/00 | (2011.01) |

(52) U.S. Cl.
CPC ...... *G01N 33/587* (2013.01); *B01L 3/502715* (2013.01); *G01N 21/6486* (2013.01); *G01N 27/44791* (2013.01); *B01L 2300/02* (2013.01); *B82Y 15/00* (2013.01); *B82Y 30/00* (2013.01)

(58) Field of Classification Search
CPC ...... B01L 3/502715; B01L 3/502; B01L 3/50; B01L 2300/02; B01L 2300/00; B82Y 15/00; B82Y 30/00

USPC .......................... 422/502, 500, 501
See application file for complete search history.

(56) References Cited

U.S. PATENT DOCUMENTS

| | | | |
|---|---|---|---|
| 6,919,009 B2 * | 7/2005 | Stonas | B01J 13/0047 205/122 |
| 8,087,768 B2 | 1/2012 | Daems et al. | |
| 2002/0012445 A1 | 1/2002 | Perry | |
| 2004/0219287 A1 * | 11/2004 | Regan | G07F 7/086 506/32 |
| 2007/0012784 A1 * | 1/2007 | Mercolino | G09F 13/20 235/491 |
| 2007/0072197 A1 | 3/2007 | Rayms-Keller | |
| 2011/0267457 A1 | 11/2011 | Weitz | |
| 2015/0111780 A1 | 4/2015 | Mercolino | |
| 2017/0307497 A1 | 10/2017 | Grier et al. | |

(Continued)

FOREIGN PATENT DOCUMENTS

| | | |
|---|---|---|
| WO | WO 2014/171767 | 10/2014 |
| WO | WO 2018/049272 | 10/2018 |

OTHER PUBLICATIONS

Nanotechnology Applications in Food and Food Processing; Innovative Green Approaches, Opportunities and Uncertainties for Global Market.

(Continued)

*Primary Examiner* — Christine T Mui
(74) *Attorney, Agent, or Firm* — Daniel Morris; Otterstedt, Wallace & Kammer, LLP

(57) ABSTRACT

A composition system which is a mixture of colloids forming a physical code is implanted into a product and later extracted and read to authenticate the product thus providing secure means to check the authenticity of the product against counterfeiting.

15 Claims, 10 Drawing Sheets

(56) References Cited

U.S. PATENT DOCUMENTS

2018/0080857 A1    3/2018  Gifford

OTHER PUBLICATIONS

Journal, International Journal of Green Nanotechnology; Physics and Chemistry, vol. 1, 2010-Issue. pp. 72-96, Published On-Line, Mar. 26, 2010.
Journal, Food Reviews International, vol. 7, 2010-Issue 1, Published On-Line, Sep. 1, 2010.
Pfeiffer et al., unpublished U.S. Appl. No. 16/203,674, filed Nov. 29, 2018, Use of Microfluidic Reader Device for Product Authentication, pp. 1-38 plus 10 sheets of drawings.
Pfeiffer et al., unpublished U.S. Appl. No. 16/203,688, filed Nov. 29, 2018, Method for Product Authentication Using a Microfluidic Reader, pp. 1-44 plus 10 sheets of drawings.
Paul J. Otterstedt, List of IBM Patents or Patent Applications Treated as Related, Dec. 20, 2019, pp. 1-2.
R. Ravichandran. "Nanotechnology Applications in Food and Food Processing: Innovative Green Approaches, Opportunities and Uncertainties for Global Markel" Intl. J. Green Nanotechnology, Physics and Chemistry, vol. 1:issue 2, pp. 72-96. Published on-line Mar. 2010.
M. Montowski. "Authenticity Determination of Meat and Meat Products on the Protein and DNA Basis." Food Reviews Intl. vol. 7:issue 1. Published on-line. Sep. 2010.

* cited by examiner

ZONAL NANOFLUIDIC ANTI-TAMPER DEVICE FOR PRODUCT AUTHENTICATION

FIELD OF THE INVENTION

The present invention relates to authentication of physical products and more specifically to a method for anti-counterfeiting products providing supply chain verification and point-of-origin tracking and means for archiving.

DESCRIPTION OF THE PRIOR ART

Embodiments of the invention improve upon previous art in the problem of providing secure means of checking the authenticity of a good. Authenticity refers to the physical truth that a particular product originated from a given supplier, and the aspects of the product's quality that are desired have been met to the standards expected by the supplier.

Counterfeit items pose a significant and growing problem with consumer-packaged goods, especially for established brands. Anti-counterfeiting measures for example, for fluid products, have focused on secure and traceable packaging or on chemical analysis of a statistical sample of the product.

Among methods used for authentication, some companies have implemented strategies such as adding high tech labeling, coatings or additives to packages that are difficult to duplicate. Although these measures help to ensure the integrity of the package, they tend to be costly, and still can be circumvented by determined counterfeiters. The expense associated with chemical analysis of a fluid product, does not allow for comprehensive verification of every package.

Publication Number WO-2018049272-A1 discloses a method for product authentication by applying an analyte encode security fluid to a substrate of the product, obtaining a sample of the fluid from the substrate, and testing the sample for the presence of the analyte.

U.S. Pat. No. 6,576,422 discloses an early attempt to identify a product involving the steps of: (1) associating with the product a marker ligand; and (2) detecting the marker ligand in the product at a later point in time as a means of identifying the product by contacting the product with a detector composition.

The detector composition comprises one or more first nucleotide sequences encoding one or more natural or synthetic ligand-dependent transcription factors, wherein said factors comprise at least one ligand binding domain, at least one DNA binding domain and at least one transactivation domain; and a second nucleotide sequence encoding a reporter gene under the regulatory control of a receptor response element or a modified or synthetic response element, and a second promoter.

The disclosed method may also employ a corepressor or coactivator or a nucleotide sequence encoding the corepressor, activator Interaction between the marker ligand and ligand binding domain is highly specific and induces a change in the expression of the reporter gene, the change producing a detectable signal identifying the presence of the marker ligand in the product. The detector composition is a cell line containing the first and second nucleotide sequences. Kits using them and products marked with specific marker ligands are useful in the method.

A more recent approach for authenticating a product is described in United States Publication Number 20150111780 that relates to a nucleic-acid based product authentication by determining authentication codes comprising target nucleic-acids using oligonucleotide probes immobilized on particulate and non-particulate substrates. The presence of the authentication code is determined using detection methods capable of particle discrimination based on light scattering or fluorescence of the particle, or by spatial resolution of oligonucleotides immobilized at specific loci on a substrate.

Publication Number WO-2014171767-A1 discloses a method for determining the authenticity of a honeybee sample by detecting a plant DNA and a honeybee DNA in the honey sample.

U.S. Pat. Nos. 8,415,164 and 8,415,165 each disclose systems and methods for: a.) securing document printing inks, paints pigments within ink cartridges or such items, and b.) authenticating sports garments or ID tags, respectively, in each case, by applying a particular nucleic acid material associated with a particular sequence of nucleic acid bases to the ink or to the garment; collecting a sample of the ink/garment having the nucleic acid; and verifying whether the ink/garment is genuine by detecting the particular nucleic acid material. The particular nucleic acid material may, in certain embodiments, be deoxyribonucleic acid (DNA).

In other embodiments the particular nucleic acid material may be ribonucleic acid (RNA). In certain embodiments the method further comprises detecting the particular nucleic acid by performing a polymerase chain reaction (PCR) of the nucleic acid material.

The use of colloidal macromolecules such as DNA as a coding object have been previously described. In cases using DNA, its chemical make-up, which allows specific codes to be synthesized and read through replication and sequencing, were used to provide a practical means of providing authentication. However, the very aspect which allows these systems to readily read-out the authentication code (i.e. the DNA base sequence) makes it facile to replicate and counterfeit. There are no degrees of freedom in changing the code at the time of authentication by physical means; the code can only be changed at the time of synthesis, and the code can be readily replicated with economical means, allowing a lower barrier to entry for counterfeiters.

Another approach to authentication is found in United States Publication Number 20170307497-A1 which discloses systems and methods for identifying fluid-phase products by endowing them with fingerprints composed of dispersed colloidal particles, and by reading out those fingerprints using a Total Holographic Characterization.

Unlike the prior art, embodiments of the present invention include a high complexity colloidal mixture comprising spherical particles (e.g. polymer beads, core-shell quantum dots, nanocrystals, etc.) and polymers (e.g. DNA) to provide a highly adaptable "physical encoding" system.

The high complexity colloidal mixtures produce codes that can be read within a reasonable time span for authentication, but the codes are physically challenging to reproduce for counterfeiting with respect to the point-of-origin user's ability to alter the code. The high complex colloidal mixtures are read using micro/nanofluidic devices as a point-of-use check of authentication.

SUMMARY OF THE INVENTION

The embodiments of the present invention describe a structure comprising a mixture of colloids, which can implanted into a product as a traveling authentication code.

A method is described in which the colloid mixture is extracted and "read" using another structure which is a microfluidic device. This microfluidic device consists of a set of nanostructured arrays which separate the colloids and read their size/marking patterns.

The degree of separation, pattern of markers, and frequency of events for the mixture constitute a unique physical code. This physical code is read and transmitted by the microfluidic device to an authentication entity which checks the reading results against the accepted value. A successful comparison implies the product is genuine. To combat counterfeiting, the present invention offers the following advantages:

The system uses a physical code, as opposed to a digital code, reducing the ability to replicate (i.e. requiring a large amount of time and cost to reproduce the constituents of the colloidal mixture).

The system uses microfluidic devices to separate the colloidal mixture, and using the resulting separation pattern as the physical code.

In the system, one is able to alter the separation pattern (the result) by changing the physical conditions under which the colloidal mixture is run by the microfluidic device. As this change can be specified at the time of authentication and can be made arbitrary, the ability to counterfeit (e.g. counterfeiting by generating digital signals that mimic the result from the microfluidic device) is reduced as it requires extensive knowledge/empirical data on the behavior of each colloid under a range of physical operating conditions.

Using a set number of colloids, a range of colloidal mixtures (and thus codes) can be produced using the same method, and using a set number of coded polymers, such as DNA, a large number of mapping codes can be produced using the same method.

A manufacturer can change the code by changing the composition of the colloidal mixture. This can be done in any time increment, from minutes to years, allowing the ability to rapidly shift the authentication code against possible counterfeiting efforts.

Only small amounts of colloidal mixture are required, allowing the possibility to embed multiple codes into the product.

The colloidal mixtures can be formulated into inks, paint, or other elements of the product, providing a way to camouflage them until they are needed.

The embodiments of the invention described above, disclose a structure and a method, which can be embodied in several different combinations of devices and processes. The invention uses a mixture of colloids (10-100 nm in diameter) as a physical code which can be implanted into a product, and later extracted and read to authenticate the product. The security of the invention against counterfeit comes from the difficult in time and costs it takes in replicating the colloidal mixture, and thus, the authentication code, versus the time it takes the manufacturer to change the mixture.

The colloidal mixture is read using a microfluidic device which separates the colloids based on size and shape, and in the case of polymer colloids such as DNA, can read patterns of markers attached to the DNA. The combination of different separated fractions and DNA markers (its mapping) constitutes the physical code.

The physical conditions under which the microfluidic device runs the colloidal mixture can be changed at the time of authentication, warding against counterfeiting due to the complexity of replicating a large number of physical scenarios.

The invention improves the state-of-the-art by using complex microscopic mixtures as a coding medium, providing a means for decoding these mixtures, and providing a security measure that is adaptable—allowing rapid changing of the authentication code against counterfeiting.

The present invention comprises a computer program product for authenticating the integrity of a product having a predetermined physical code embedded therein, said computer program product comprising a computer readable storage medium having program instructions embodied therewith, said program instructions readable by a microfluidic device to cause said microfluidic device to the authenticity of a product and to perform methods defining the authenticity of the product as described in detail above and hereinafter.

A further embodiment of the present invention, comprises a computer-implemented method for generating data resulting from passage of a structure (composition) comprising a mixture of colloids as a physical code through a microfluidic device, which physical code can be implanted into a product, and later extracted and read to authenticate the product.

DETAILED DESCRIPTION OF THE DRAWINGS

DESCRIPTION OF THE PREFERRED EMBODIMENT

Figure 1:
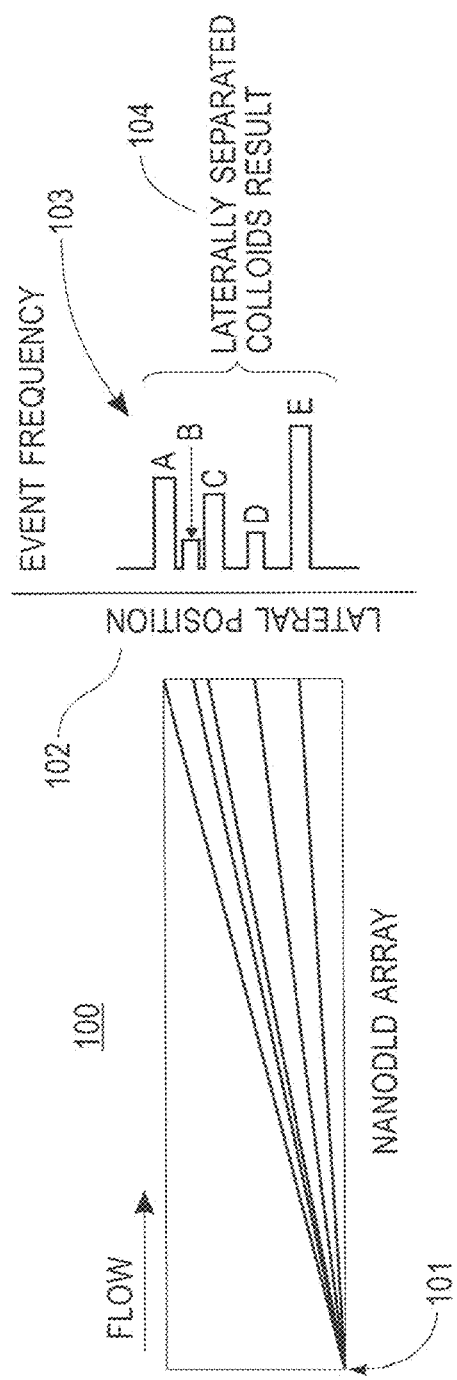
FIG. 1 depicts an array schematic and results showing event frequency for laterally separated colloids.

The instant invention is a system for authenticating a product's origin, properties and intended transaction history. The system is devised to reduce the possibility of counterfeiting by providing a high barrier of entry, both in time and material, to copying the authentication code.

It is intended that the constraints on time/material for counterfeiting the code (and thus the product) are much greater than the ability of the original producer to change the authentication code, and thus reduce the incentive for duplicity.

A brief summary of an embodiment of the present invention is as follows: a physical authentication code is made from a mixture of small particles which can be attached to a product as a traveling security measure.

At any time, a person can verify the authenticity of the product by collecting the authentication code and running it through a prescribed microfluidic device which "reads" the physical code and transmits the result back, i.e. through wireless communication, to the original manufacturer, or an entity maintaining the authentication process.

The science of microfluidics deals with very small volumes of fluids, down to femtoliters (fL) which is a quadrillionth of a liter. Fluids used in a microfluidic device, i.e., a chip, behave very differently on the micrometric scale than they do in everyday life.

An authentication code ("code") consist of a mixture of colloidal particles, which particles generally are a substance microscopically dispersed evenly throughout a solution i.e., a solvent. The dispersed-phase particles can have a diameter between about 5 and 200 nanometers.

For the purposes of this invention, the solution composition—comprising a solvent plus any number of diverse colloids—may also be referred to herein as a "structure". Practically this is some form of liquid solution/colloid (fluid) combination, specially formulated, that could either be used as-is, or deposited onto a product/packaging, such as an ink.

Colloidal particles as found in the present system consist of two types:

1.) Hard-bodied colloidal particles of any variety of shapes (spherical, oblong, rod, branched, prismatic, etc.), sizes, and constructs (single crystals, aggregates, self-assembled complexes, etc.). The properties of shape, size and construction are the major factors for the code mixture. A set of colloids which have a wide span of values for the aforementioned properties is required for producing a code.

Hard-bodied colloidal particles that are suitable for use in the present invention are formed using typical nucleation-growth chemistry synthesis, emulsification and filtration for polymer beads known in the prior art.

The code comprises the types of colloids as mentioned above.

The colloids can constitute: 1.) any particulate matter ranging in diameter from 1-1,000 nm for nanoscale/mesoscale colloidal systems, or 1-100 μm for microscale systems.

The colloids can include metal and metal oxide particles, quantum dot semiconductor particles, organic layer stabilized metal core nanoparticles, polymer particles and microbeads, pigment particles, nucleic acid origami, small molecule aggregates, dsDNA fragments, synthetic polymer fragments, self-assembled protein capsules or complexes, deactivated and stabilized cells, pollen, deactivated spores.

The colloids can be of any number of shapes, including spherical, rod-shaped, polyhedral, etc. The colloids can have various properties such as fluorescence, non-linear photo-effects, phosphorescence, elasticity, opto-mechanics, photolysis, photo-aggregation, photo-absorbance, magnetism, etc. The ratio of the diverse colloids in the formulation which ranges between 0 to $1 \cdot 10^{20}$ particles/mL, preferably between $1 \cdot 10^5$ and $1 \cdot 10^{14}$ particles/mL.

2.) Polymeric particles comprising nucleotide-based polymers which can readily synthesized and encoded with specific base sequences. The DNA base sequence can be custom selected to allow the attachment of markers to specific, selected sites along the DNA chain.

Nucleotide particles that are suitable for use in the present invention are preferably DNA, RNA, or any similar polymer created from a family of double-helical DNA-like polymers where one of the four normal bases is replaced with various cationic, anionic or neutral analogs.

These markers consist of colloidal particles physically or chemically attached (bound) to the DNA chain at the selected site(s). Suitable colloidal marker particles for labeling DNA for mapping include fluorescently labeled cDNA fragments, fluorescently labeled DNA constructs (specifically, hairpins, origami) with appropriate insert tails, fluorescently labeled binding proteins or complexes, sequence-specific intercalator dyes or pigments.

These marker particles are selected to be compatible with optical or electrical detection within the microfluidic reader, as described below. The particular sequence of markers along the DNA chain, for a particular chain sequence and chain length, consists of a second tier of physical encoding. Multiple marker-bound chains can be added to a single code to increase the complexity depth.

Codes are prepared by mixing different colloids, with different properties, in set ratios. The code value consists of the volume fractions of each colloid, and the properties of each colloid, recorded collectively. A producer, or an entity that produces codes, prepares a unique code by mixing well-defined colloids together and recording the fractions/properties for that code batch.

In addition, additives, including: emulsifiers, anti-coagulants, blockers against non-specific adsorption, anti-photobleaching agents, antibiotics, stabilizers, anti-foaming, thickening or thinning agents, salts, pH buffers, sensitizers, and agents for allowing reconstitution of the formulation into solution can be added to increase the physical complexity of the code.

The code requirements include stability under the conditions of the product's transactions, across the lifetime of the product and the ability to re-dissolve the code to a reproducible concentration under set conditions. All particles must be charged and have the same charge polarity (e.g. negative) for electrophoresis (see below).

The code mixture is attached to a product, and travels with the product through the lifetime of transaction with the product (e.g. shipment, operation, storage). Attachment can include numerous methodologies: painted on the surface of the product, adsorbed into the product or its packaging or into a special tag or location on the product, sealed in a small case or capsule on the surface or inside the product, etc.

The code location can be made conspicuous and concerted, or hidden with the product/packaging and thus requiring the location of the code to be given by the authentication entity at the time of authentication.

Multiple codes can be incorporated onto a product, allowing the ability for the authentication entity to randomly select a given code for a given authentication, adding further variability and thus security to the process. False codes can be made conspicuous while true codes hidden to act as "blinds" against counterfeiters.

The lack of a code on a product constitutes the first security check for authenticity. The requirement to obtain the location of a hidden code constitutes an additional security check.

Embodiments of the present invention utilize microfluidic devices. Microdevices exploit the physical and chemical properties of liquids and gases at the microscale.

A microfluidic chip is a set of micro-channels etched or molded into a material (glass, silicon or polymer such as PolyDimethylSiloxane [PDMS]). The micro-channels forming the microfluidic chip are connected together in order to achieve the desired features (mix, pump, sort, or control the biochemical environment).

The microfluidic chip is elaborated so that the incorporated automation allows the user to generate multi-step reactions requiring a low level of expertise and a lot of functionalities. The microsystems execute functions that extend from detecting toxins to analyzing DNA sequences or creating inkjet printing devices.

Microfluidic devices offer several benefits over conventionally sized systems. Microfluidics allows the analysis and use of less volume of samples, chemicals and reagents reducing the global fees of applications.

Many operations can be executed at the same time thanks to microfluidic compact size, shortening the time of experiment. Microfluidic devices also offer an excellent data quality and substantial parameter control which allows process automation while preserving the performances. They have the capacity to both process and analyze samples with minor sample handling effort on the part of the technician.

This network of microchannels incorporated into the microfluidic chip is linked to the macro-environment by several holes of different dimensions hollowed out through the chip. It is through these pathways that fluids are injected into and evacuated from the microfluidic chip.

Fluids are directed, mixed, separated or manipulated to attain multiplexing, automation, and high-throughput systems. The microchannels network design must be precisely elaborated to achieve the desired features (lab-on-a-chip, detection of pathogens, electrophoresis, DNA analysis etc.).

To accurately manage fluids inside the microchannels, specific systems are required. These elements can either be found embedded inside the microfluidic chip, such as Quake valves, or outside of it, like in the case of pressure controllers.

To authenticate a product, the microfluidic reader device described above is used. The microfluidic reader consists of: 1. a micro/nanofluidic chip; 2. a fluid for dissolving the code; 3. an interface for loading fluid into the device/chip; 4. a detector(s) embedded in the chip and/or interfaced to the chip; 5. a housing for protecting the chip/detector and providing interfacing of fluids to the chip; 6. a driving mechanism for moving fluids/colloids through the chip; 7. a power source; 8. a controller (microcontroller, computer, etc.) for running the chip/detector 9. a wireless transceiver for sending/receiving data; 10. a user interface for operating and monitoring the authentication process.

The microfluidic reader operates by running the code, dissolved in a fluid, through the microfluidic chip and recording the individual colloids in the code. The recorded output of the code, the "result", is stored digitally and transmitted to the authentication entity through the transceiver.

To prepare the code for the reader, several options are possible; the location with the code can be removed and placed in a preset volume of fluid to dissolve the constituents, a special tool or applicator with fluid can be used to extract the code directly from the product, capsules, or packets of code can be loaded directly into the reader interface where their contents are opened and processed. It is required that the fluid (with code) contacts and wets into the microfluidic chip, which primes the chip for reading the code.

The microfluidic chip can consist of two components: 1) a nano-Deterministic Lateral Displacement (DLD) pillar array (nano-DLD array), 2) a DNA mapping array.

Deterministic lateral displacement (DLD) is a microfluidic particle-separation technique that makes use of successive bifurcations of the laminar flow around an array of regularly arranged pillars. This technique enables one to separate nanometer to micrometer-sized particles around a critical diameter called Dc. Several models are available to anticipate the value of De according to the geometrical characteristics of the DLD array, such as the pillar interspacing, the array rotation angle, the shape and the orientation of the pillars. The separation phenomenon is based on steric effects around an array of shaped micro-pillars: particles larger than a critical size are laterally displaced by the pillars whereas smaller particles follow a global straight path.

The nano-DLD array consists of a microchannel into which a lattice of pillars is fabricated and which is wet with fluid. The lattice is fabricated with an asymmetry which provides the means of separating particles laterally across the array according to size and shape in a continuous flow mode as described in disclosures found in U.S. Pat. Nos. 9,636,675 and 10,058,895, the contents of which are hereby incorporated by reference herein.

The depth, pitch, gap size, pillar shape, pillar diameter, row-shift offset and all other geometric parameters of the array can be chosen to select for a specific separation spectrum of particles according to size.

In general, for a given array design, particles larger than a critical size are displaced laterally within the array at varying angles (depending on the particle size) while particles smaller than the critical size flow through uninhibited.

The steady-state lateral spatial distribution of a mixture of colloids of differing shape, size and volume fraction constitutes a physical encoding of information into a specific, reproducible pattern that can be observed and recorded. This is the first tier of information stored in the code and which is ascertained by the reader.

FIG. 1 at 100, illustrates a formulation (solution) of colloids of different sizes being injected into a nano-DLD in a focused jet 101 and how they displace 102 into a "spectrum" of peaks 103. The degree of displacement (the lateral position) 104 for a given colloid is determined by the nano-DLD array's geometry and the geometry and the mechanical properties of the colloid itself.

The size and spread of the peaks is determined by the concentration of the colloid, diffusion in the array, and the amount of signal received from each colloid for a given detection method (e.g. scattering, fluorescence, etc.). The accumulated spectrum of peaks 103 at the end of the array constitutes a unique pattern that is determined by the formulation and nano-DLD device, and can be used as a physical-based authentication code, inherent to the properties of the formulation.

The speed at which colloids are transmitted through the array affects the degree of lateral displacement. In addition, hard-bodied spherical particles and polymers have anti-correlated responses to flow velocity: at slow flow, polymers such as DNA almost completely displace laterally while spherical colloids are diffusion dominated and have no clear displacement. At high flow, polymers have little to no displacement, while spherical colloids attain their maximum lateral displacement.

Controlling the flow velocity causes a proportional change in the degree of lateral displacement of a given colloid, allowing another dimension of information to be encoded. The basis of affecting polymers (such as DNA) separation based on speed has been described in U.S. Pat. No. 9,835,538, the contents of which are hereby incorporated by reference herein.

Figure 2:
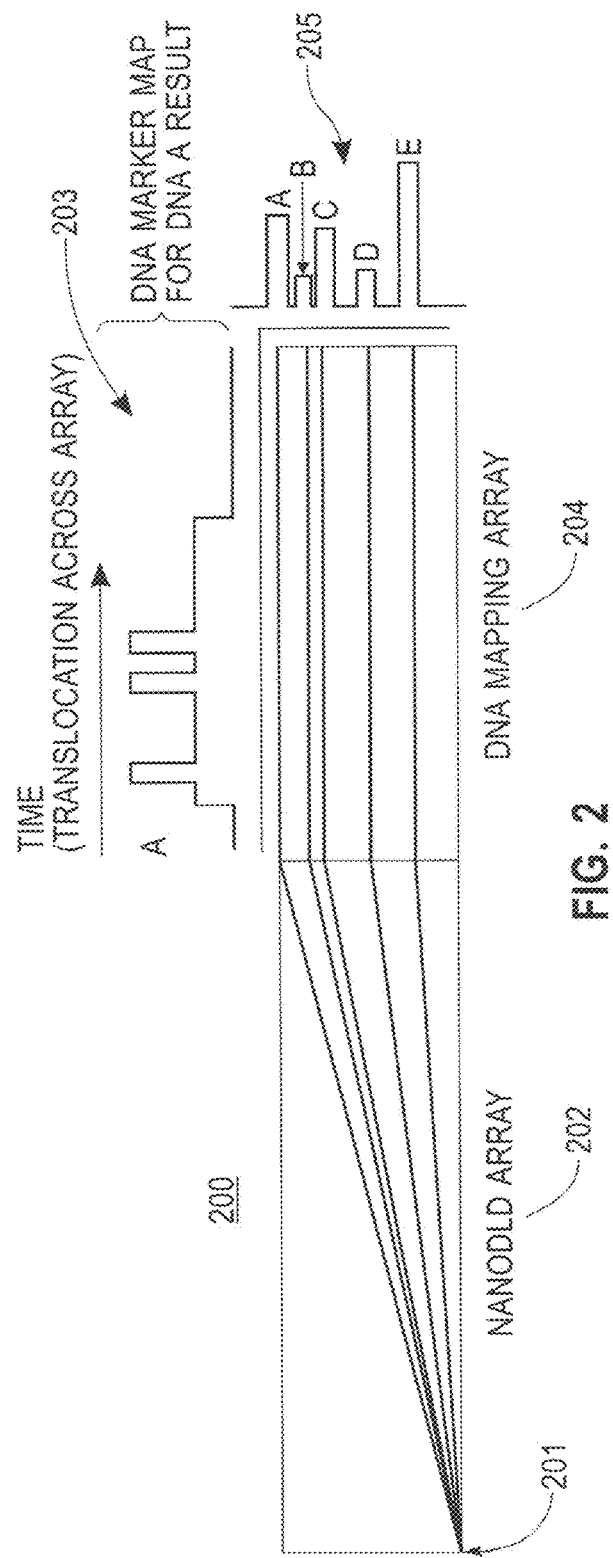
FIG. 2 depicts an array schematic for a nano-DLD array and a DNA mapping array results showing a time translocation variable across the array for the DNA marker map.

FIG. 2 at 200 illustrates a fluorescently backbone-labeled DNA formulation being interrogated by both a nano-DLD array and a DNA mapping array. The nano-DLD emanating from focused jet 201 forms an array 202 that ultimately forms a spectrum of peaks 203 with each peak determined by the length and bound species on the DNA fragment. Each DNA fragment is then fed into a set of nanochannels (mapping array) 204 which elongates the DNA into a stretched strand (line) which can be read along the channels. The length of the fluorescent line indicates the fragment length. The presence of any site-specific fluorescent markers constitutes a unique pattern 205 that is determined by the formulation and the analysis devices.

The nano-DLD array 202 and DNA mapping arrays 204 do not have to be directly coupled as illustrated; they can be run in two separate stages, with the output of the nano-DLD array being read-out first and then remixed together and fed into the DNA mapping array.

Figure 3:
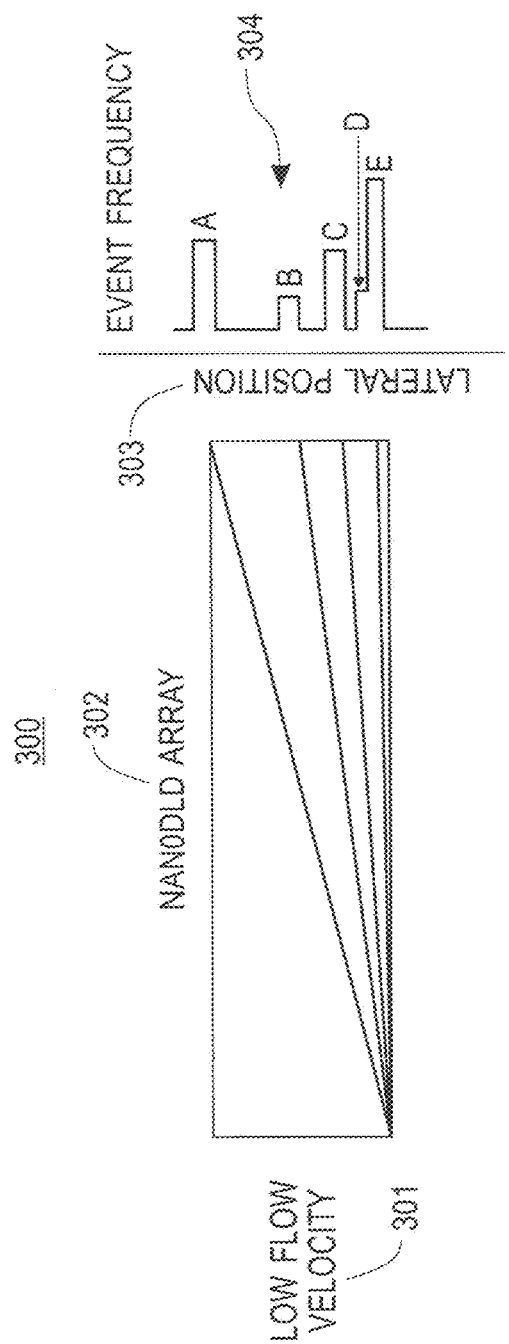
FIG. 3 depicts readout of code results by the use of low flow velocity.
Figure 4:
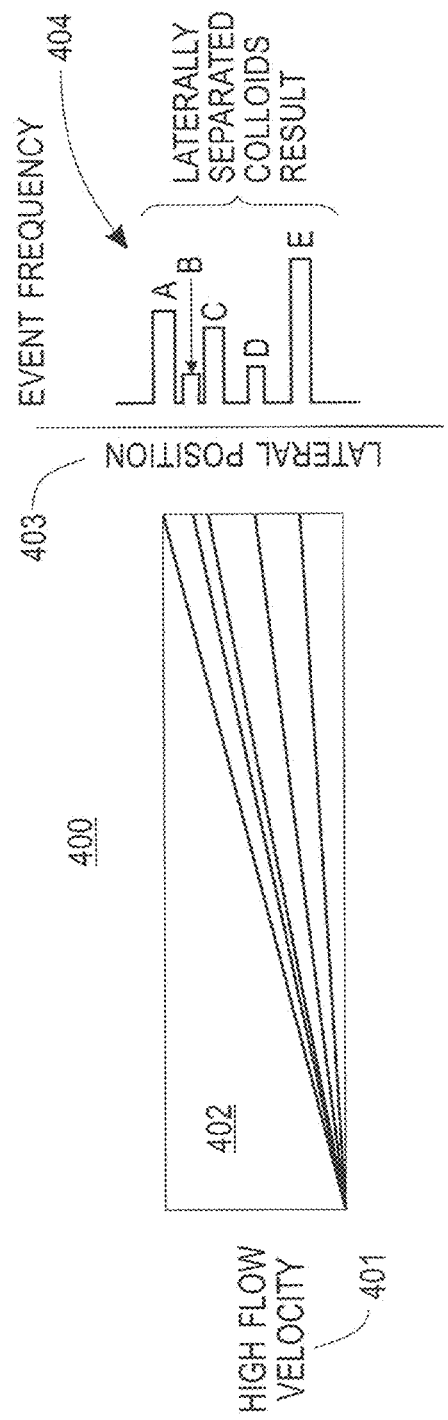
FIG. 4 depicts readout of code results by the use of high flow velocity.

FIGS. 3 & 4 illustrate how fluid velocity can be used as a handle to add additional complexity to a code formulation. More particularly, FIGS. 3 and 4 at 300 and 400 respectively, illustrate the impact that changing the flow velocity has on the results obtained when authenticating a code that has been embedded or attached to a product.

FIG. 3 at 300 illustrates a colloid formulation running through a nano-DLD array 302 at a low flow velocity 303, showing a particular lateral distribution of colloid peaks 304.

The use of low flow velocity 301 on the various nano-DLD array elements 302 results show a lateral positions readout 303 as recorded in the event frequency bar chart 304. The amplitude of the datum reflected in each of bars A through E of bar chart 304 reflects the value of each datum.

FIG. 4, at 400 by contrast, illustrates the same colloid formulation as that used in FIG. 3, running at a higher flow velocity 401, which shifts the peak distribution 402, showing a particular lateral distribution of colloid peaks 403.

The use of high flow velocity 401 on the various nano-DLD array elements 402 results show a lateral positions readout 403 as recorded in the event frequency bar chart 404. The amplitude of the datum reflected in each of bars A through E of bar chart 404 also reflects the value of the datum. Bar chart 404 depicts the laterally separated colloid result of the code analysis.

The causes for the peak distribution shift have been illustrated in the literature, and included reduction in the effect of diffusion on the displacement process, and shear-induced deformation of the colloid causing a perturbation in its trajectory through the array. By using velocity dependence, a single fluidic code can be expanded into several fluidic codes by adding the additional parameter of flow velocity, or in addition, the robustness of an authentication can be increased by requiring multiple flow velocities to be probed.

To read the lateral displacement of a code mixture in the nano-DLD, optical or electrical methods can be employed. For an optical method, all colloids and DNA markers must emit light (e.g. fluorescent).

An optical detector, with sufficient spatial temporal intensity resolution, would consist of an excited light source and a photodetector array which can be used to line-read the lateral distribution of colloids based on the fluorescence intensity. Multiple excitation wavelengths can be used for different fluorescently tagged colloids, allowing another dimension of information encoding. The colloid distribution can be detected electrically using an array of channels downstream of the nano-DLD array to bin the colloid output.

Each channel is built with an electrical detector (e.g. transverse electrodes, field effect transistor, etc.). The presence of colloids in the channel is transduced into an electrical signal, and the combined signals from each channel are concatenated to describe the distribution of colloids laterally across the nano-DLD array. The lateral distribution is transcribed into a digital signal, and forms a Tier 1 result.

The DNA mapping array consists of a set of nanochannels, running in parallel, which are wet with fluid and which allow colloid particles to flow through the channels. When DNA is flowed into the channels, due to the size constraints, the polymer must elongate into a linear chain. This unfolding of the coiled state presents the polymer as a linear sequence, with its markers sequentially spaced along its length. Note there can be two read frames, forward or reverse, depending on which end of the DNA enters the nanochannel first, with respect to the flow.

The specific marker sequence on the elongated DNA chain is termed the "map," and constitutes a physical encoding of information into a specific, reproducible pattern that can be observed and recorded. This is the second tier of information stored in the code and which is ascertained by the reader.

To read the DNA map ("mapping") of a code mixture in the nano-DLD, optical or electrical methods can be employed.

For an optical method, all DNA markers must emit light (e.g. fluorescent).

An optical detector, with sufficient spatial temporal intensity resolution, would consist of an excited light source and a photodetector array which can be used to line read the lateral distribution of colloids based on the fluorescence intensity.

The basic technology of DNA mapping with fluorescence has been previously described in patent literature. Multiple excitation wavelengths can be used for different fluorescently tagged markers, allowing another dimension of information encoding. The marker distribution can be detected electrically using an array of electrical detectors (e.g. transverse electrodes, field effect transistor, Coulter counter etc.) downstream of the nanochannels to read the linear DNA map.

The presence of DNA, and the presence and sequence of markers along the DNA, in the channel is transduced into an electrical signal as the DNA flows through a nanochannel. The length and spatial distribution of markers along a DNA chain is transcribed into a digital signal, and forms the Tier 2 result.

Note, the DNA can be threaded forward and in-reverse within the nanochannels by reversing the flow to allow multiple-reads of a given DNA/marker sequence.

The microfluidic chip can be configured to run Tier 1 or combined Tier 1+Tier 2 results. For codes consisting of hard-bodied spherical particles+DNA, in generally only Tier 1 (i.e. nano-DLD only) results can be made, as the size range applicable to nano-DLD would clog nanochannels necessary for DNA mapping. For codes consisting of only DNA, Tier 1+Tier 2 results could be run.

A generic chip consists of an entrance, where the code fluid is introduced, along with a series of nano-DLD or nano-DLD/DNA mapping arrays. The end of the last array may also consist of capillary pumps or open holes to allow capillary wetting of the fluid into the device. Alternatively, the chip can be pre-wetted and the interface simply makes contact between the code fluid and the liquid inside the chip.

To run the microfluidic chip and obtain the result, electrophoresis is used.

Electrophoresis, which is one of the electro-kinetic phenomena observed in colloidal systems, is the motion of charged colloidal particles in a liquid medium under an applied electric field. Charged colloidal particles in the stationary state move with a constant velocity as a result of the balance between the applied electric field acting on the particles and a viscous resistance exerted by the liquid on the particles.

In the case where the magnitude of the applied electric field E is not very high so that the particle velocity U, which is called the electrophoretic velocity, is proportional to E in magnitude. The ratio of the magnitude of the velocity U to that of the applied electric field E is called the electrophoretic mobility $\mu$, which is defined by $\mu=U/E$ (where $U=|U|$ and $E=|E|$).

In the case of hard particles without surface structures, the electrophoretic mobility $\mu$ depends on the zeta potential $\zeta$ of the particle. The zeta potential is defined as the potential at the slipping plane, at which the liquid velocity relative to the particle is zero. If the slipping plane is located at the particle surface, the zeta potential $\zeta$ becomes equal to the surface potential $\psi_o$ of the particle. In the case where $\zeta=\psi_o$ and where particles are of spherical or cylindrical shape, the surface charge density $\sigma$ of a charged particle can be calculated from the particle surface potential $\psi_o$.

In the case of soft particles, that is, e.g., hard particles covered with an ion-penetrable surface layer of polyelectrolytes, the concept of zeta potential loses its meaning and the Donnan potential in the surface layer plays an essential role in electrophoresis of soft particles.

Electrodes at the beginning and end of the chip are energized and set up an electric field gradient which drives the migration of the colloid mixture through the arrays. This generates a flow of colloids which powers the lateral displacement in the nano-DLD array, and/or the elongation and translocation of DNA through the mapping arrays. The field intensity and polarity can be adjusted to affect the speed of flow and direction of flow, respectively. While the colloids are flowing through the arrays, the detector observes and records the output as the result. The result is transmitted digitally to the authentication entity, which stores the key relating the product to its correct code.

Cross-checking of the transmitted result to the stored correct value provides the authentication.

To avoid the ability of a counterfeiter to pre-sample a code and then artificially construct the result for transmission, different physical conditions can be arbitrarily chosen and run on the microfluidic device, per the instruction of the authentication service, increasing the number of possible combinations of results, and reducing the probability of a counterfeit from artificially construction or guessing the correct code.

Physical conditions can include different flow speeds, temperature, viscosity of the fluid, type of fluid, which code is used for authentication. The necessary hardware for each physical condition can build into the chip/reader to allow randomized run states.

The key feature of the invention is the complexity of the code. To reconstruct the entire code requires the synthesis of colloids with precise properties, formulated to the correct concentration and the ratio of colloids.

Figure 5:
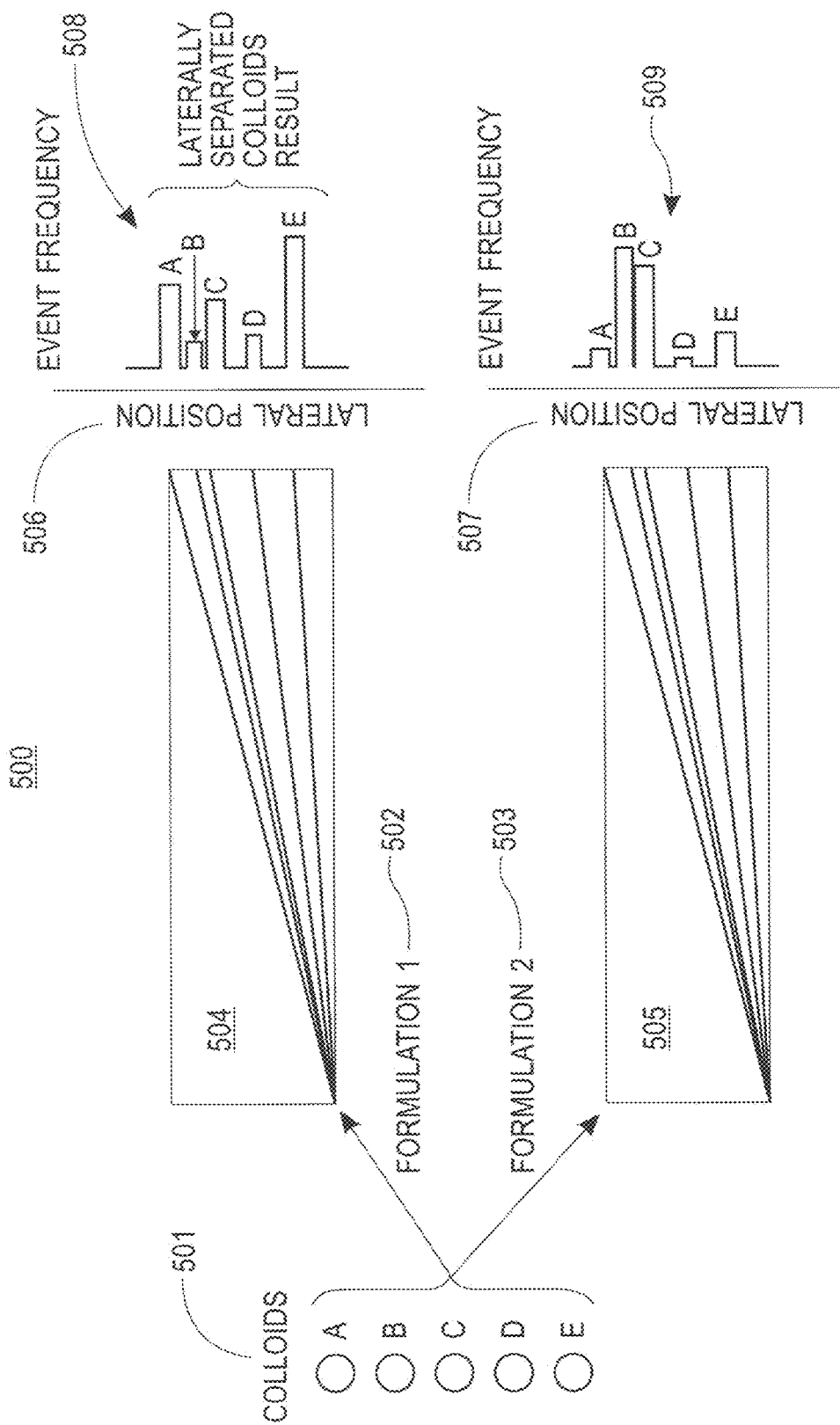
FIG. 5 depicts examples of changing results by changing the colloid formulation concentrations/ratios.

FIG. 5 at 500, depicts an example of changing the complexity of the code by changing formulation concentrations and the ratio of colloids 501. Formulations 502 and 503 each having different ratio of colloid constituents, are run as shown in nano-DLD arrays 504 and 505 and result in different lateral positions 506 and 507. A comparison of event frequencies 508 and 509 illustrates the different end result obtained when varying the formulation concentration and the ratio of colloid constituents. FIG. 5 illustrates how a single pallet of different colloids can be used to generate different code formulations.

Five colloids (A, B, C, D and E) 501 of different sizes/shapes are mixed into two formulations, 1.) 502 and 2.) 503, with different ratios (concentrations) of each colloid. Running each formulation through a nano-DLD arrays 504 and 505 leads to the same displacement locations for each colloid but different peak intensities for each formulation.

The combination of lateral location and peak intensity identifies each formulation as a unique code. Using this system, a manufacture can modulate at will the ratios of colloids in a formulation periodically over time spans of years, months, weeks, days, hours or shorter, to generate different codes without expending extra cost on making more colloid sizes/shapes.

In addition, since the conditions of running the code can be altered at the time of authentication, a full reconstruction of the code is extremely challenging and requires time and cost. As the code can be arbitrarily formulated rapidly by the source manufacturer, as noted above, codes can be changed at will.

Thus the time to reconstruct the code by a counterfeiter greatly exceeds the period over which the code is changed. This provides security against counterfeiting, as the cost and time for mimicking a product is too high to warrant the investment.

Each code formulation, at the time of production, is recorded and stored for authenticating against results in the future. Codes can be stored in the same conditions at those intended for the product. Code results can be recorded at the time of formulation on standardized readers, and the results stored digitally for authentication in the future. Code results may need to be processed at the time of receipt at the authentication entity to resolve the information. This could involve deconvolution of time series taken for the DNA mapping, cross-correlating lateral displacement and mapping data for a given DNA chain.

An algorithm, customized to the particular coding formulation and code type can be implemented to analyze and compare the transmitted result to the correct value.

The steps for preparing a formulation for application to a product are:

1. Acquisition or synthesis of requisite colloids, e.g. nucleation-growth chemistry for nanocrystal synthesis, emulsification and filtration for polymer beads, solid phase synthesis or gene expression for DNA or RNA followed by bioconjugation of markers.

2. Property analysis of each colloid is conducted to have a clear record of the colloidal parameters for future authentication. This includes at a minimum, optical properties, identification of colloids, size of colloids, length of polymer strands, and their calibrated behavior in the selected nano-DLD and/or DNA mapping arrays.

3. Identify the complexity of the code as the number of colloids in the formulation directly relates to the density of information, and hence the difficulty to replicating the code. The number of colloids used will be a balance of the frequency of having to change the code, the importance of the goods being protected, the expected sophistication of any counterfeiting effort against the code, and the economics of producing the formulation.

4. The code consists of the types of colloid, the properties of each colloids, and the concentration of each colloid in the formulation. In addition, the formulation quantity, the type of carrier solvent used, and the need for any additional additives are considered.

5. A list of each colloid component is generated (e.g. by a designer or computer). The list can be compiled randomly, or according to an algorithm, or from a pre-compiled set from a list.

The aforementioned list is selected for a particular time, location, and/or product, and represents the contents of the code for that specified period.

6. A technician or machine dispenses and mixes the blend to form a formulation.

7. The formulation is aliquoted into any required receptacle (e.g. capsule or pouch) and then transmitted to the required good, or stored until time of use. In the case of a direct application of the code (e.g. as a pigment), an ink jet type printer can be used to automatically apply the code to the desired location on the product. Additionally, the application can be built directly into the printing line for the packaging or product, to automatically apply the code.

The steps for authentication are: 1. User locates the code on the product. In the cases where the code has been hidden, or several codes are present, the user first contacts the authentication entity, which in turn provides information on where the code is located and which is to be used for that authentication.

2. The user removes the code from the product. This can consist of any number of methods, depending on the way the code is applied. If the code has been directly applied to the product, it may require removing a piece of the product and dissolving the code into a pre-specified quantity of fluid. If the code is stored in a pouch or capsule, this can be directly removed. Special equipment may be specified that improve the accuracy and reliability of retrieving the code from the packaging.

3. Load the code into the reader. In the case of a seal pouch or capsule, this may be directly loaded into the reader without further handling steps. In the case of having to reconstitute or re-dissolve the code, this may involve injection (e.g. by syringe, applicator, pipet, pouring, etc.) into the reader, or into a special cartridge or hander plate which is then inserted into the reader.

4. Reader loads the code into the microfluidic chip. This can be done by capillary wetting, direct pressurization, electrophoresis, or any other method that can impel the colloids in the code fluid into the microfluidic device.

5. User sets the reader operation. This may involve the user entering several input parameters (e.g. time, date, product, authorization information, etc.), may involve the authorization entity remotely activating the reader, or sending information (e.g. authorization information), or an automatic program stored on the reader.

6. The reader checks there is a secure communication line with the authentication entity, e.g. through encrypted wireless communication.

7. The reader begins the processing. The code fluid/sample is moved through the nano-DLD and/or DNA mapping arrays within the fluidic chip and processed. The reader controls the drive force (e.g. electric field for electrophoresis) to maintain the correction operational speed and stability of the code.

8. As each colloid, or as stream of colloids, in the code fluid passes through the microfluidic chip, the chip (and any auxiliary electronics or detectors) read the lateral displacement and mapping information and store it in the controller.

9. The controller can pre-process stored result information, if required.

10. A code is run until either a sufficient amount of time has passed, a sufficient quantity of data has been collected (e.g. number of counts, threshold of counts, resolution accuracy obtained, confidence band obtained, number of expected results obtained, no unique results observed over a set time span, etc.) or the entire code fluid has been processed.

11. The stored result is then encrypted and transmitted to the authentication entity.

12. The authentication entity receives the result and checks the data directly with the stored, expected value.

13. If there is a discrepancy, the authorization entity may request the code rerun, or may perform a test of the same code kept in storage, run under the same conditions.

14. If the code result matches the stored value, the authorization entity transmits back a positive result, indicating the good or product is authentic.

15. If the code result does not match the stored value, and cannot be verified by further checking, the authorization entity transmits back a negative result, suggesting the good or product is counterfeit or the code has been tampered with.

Figure 6:
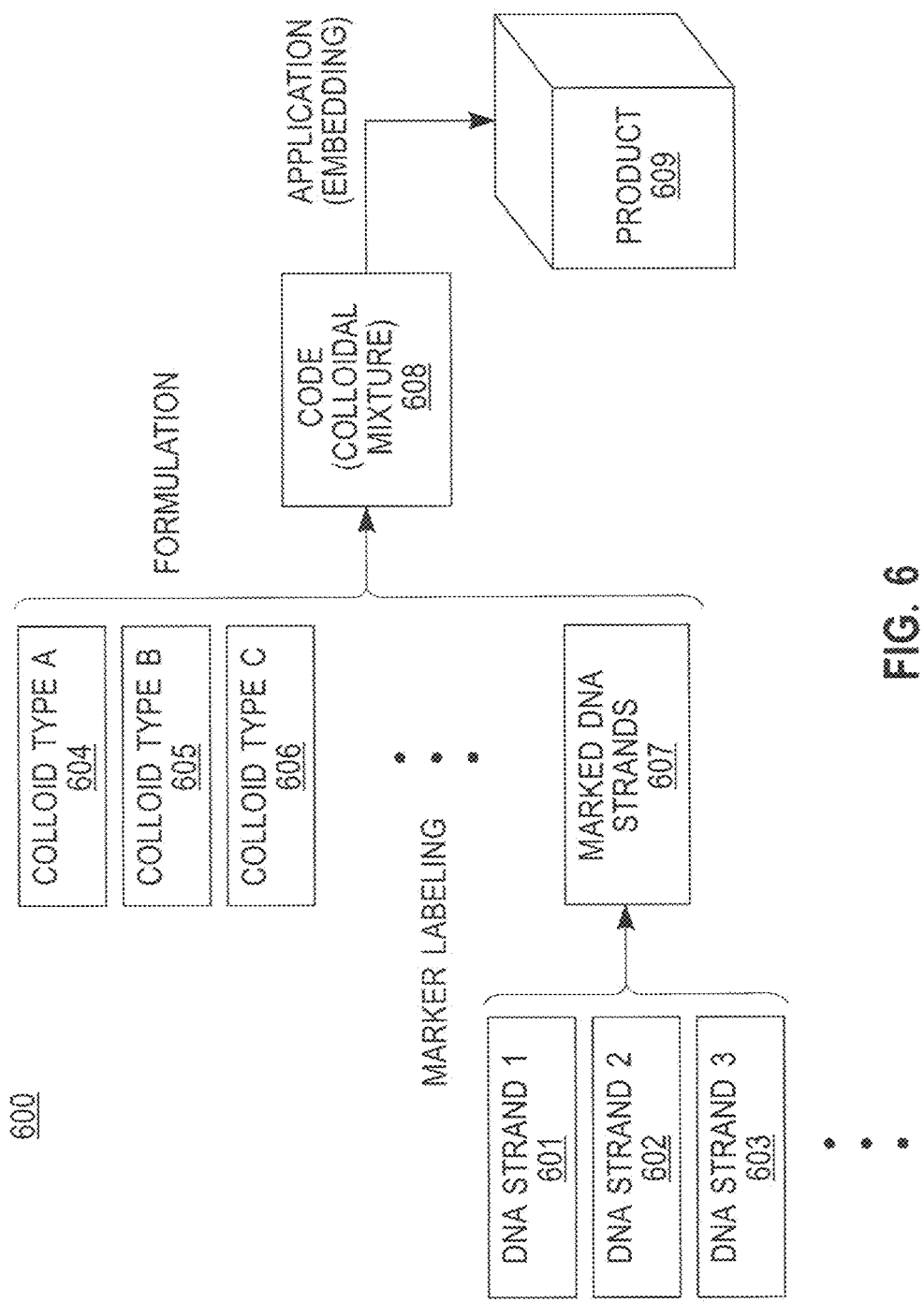
FIG. 6 is a block diagram showing the sequence of steps in the formulation of code and application of same.

FIG. 6 at 600 shows a flow diagram for formulating and applying the code fluid. In a generic protocol, multiple DNA strands (601 (1), 602 (2) and 603 (3) . . . ) and their final concentrations in the code fluid are selected and labeled with specific markers. The markers can be any number of biological constructs, including small oligomers with fluorescent beads, site-specific binding proteins with fluorophores, etc. The DNA/marker pattern and concentration of each DNA strand length is registered.

A set of colloids 604, 605, and 606 of known size, shape, polydispersity, and concentration is selected and their properties registered. The DNA and colloid sets can be mixed to form a final formulation, or either one used separately for the code fluid. The code fluid mixture can be supplemented with any number of additives to improve anti-coagulation, non-specific adsorption, photo-bleaching, antibiotics, shelf-life stability, reconstitution from dried state, adhesion, etc. The entire recipe of the formulation is registered as a "master copy" of that formulation.

The code fluid is then applied to the product. The code fluid can be embedded in several ways, including as a small liquid sample in a blister or package, as a dried ink or powder, etc. The product, location, methods, time and date of embedding, and any other pertinent information for authentication are registered. The entire accumulation of registered information is then stored as a "master copy" in a protected sever (or other storage media) which is used to future authentication by users afield.

More specifically, the steps of preparing a Tier 2 formulation are shown at 600 in FIG. 6. Synthesized nucleotide-based DNA polymers 601, 602, 603 have been encoded with specific based sequences that are custom selected. At step 607, markers, consisting of colloidal particles 604, 605 and 606 are attached (bound) to specific sites along the DNA chain. At 608, a solution is blended with the DNA that has the particular sequence of markers along its chain, thereby forming the "code."

An aliquot part of the code (the formulated colloidal mixture) that was duly prepared is then applied to, or embedded into product 609 to allow its authenticity to be determined later.

Hard bodied colloidal particles of diverse types 604 (A), 605 (B) and 606 (C), respectively, embodied within Tier 1, are blended at 608 with solution, and after the mixture is properly formulated, applied to the product.

Figure 7:
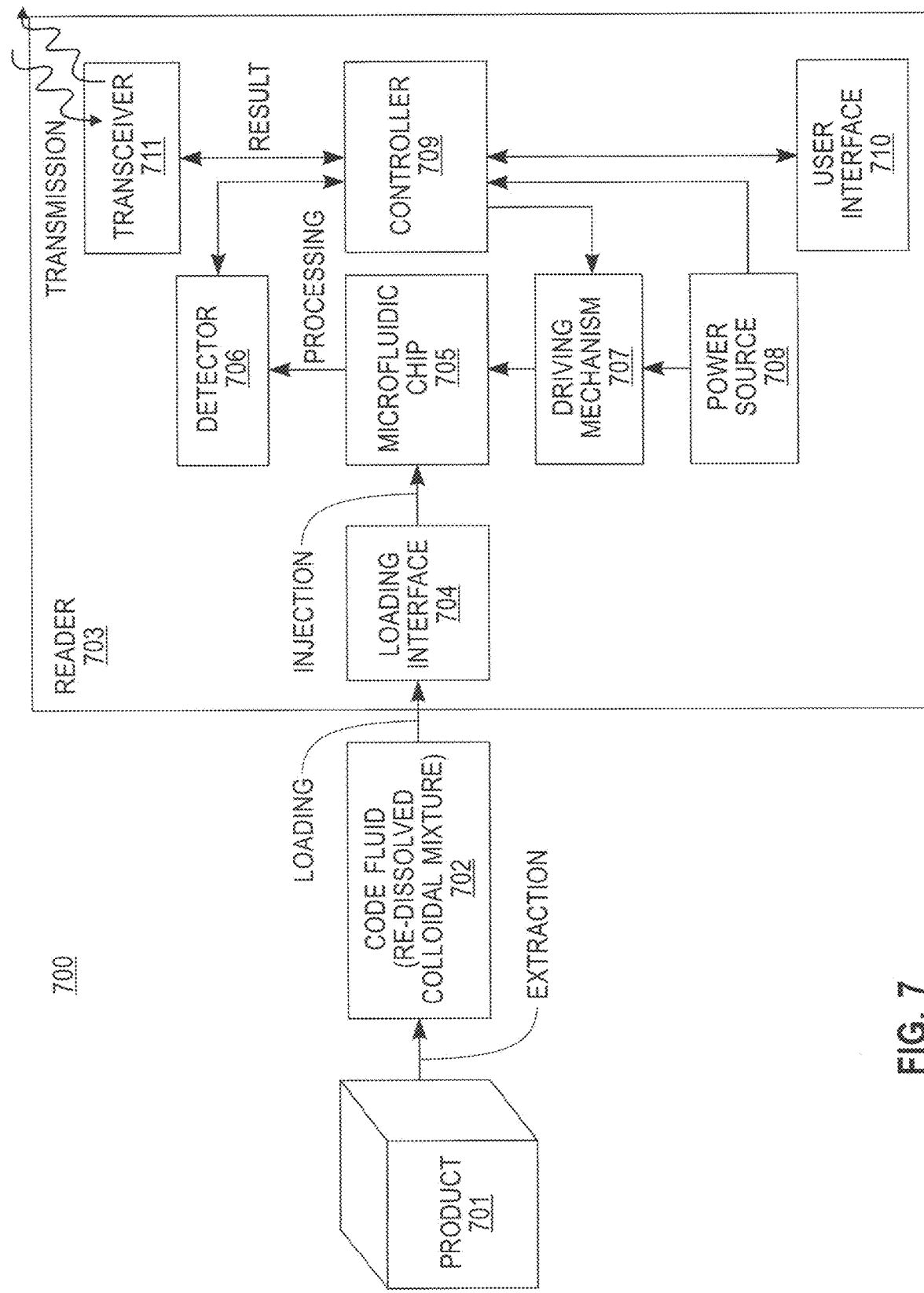
FIG. 7 is a schematic of running code in a reader.

FIG. 7 at 700, illustrates the manner by which the code is extracted from an article using the Reader used in accordance with embodiments of the present invention.

For purposes of the present invention, the term "Reader" includes the plurality of elements disclosed above, including loading interface 704, microfluidic chip 705, detector 706, driving mechanism 707, power source 708, controller computer 709, user interface 710, and transceiver 711.

Product 701 to be inspected is an entity that has had a specific code embedded in or attached to it. The embedded or attached code is extracted from product 701 and is formulated to result in a re-dissolved colloidal mixture 702 as a code fluid. Code fluid 702 is loaded into reader 703.

More particularly, FIG. 7 shows a flow diagram of components for the read-out of code fluid. After product 701 is authenticated and inspected, code fluid 702 is extracted by any number of means (punctured blister, re-dissolved from a conspicuous or hidden ink). The code fluid is then loaded into Reader machine 703.

As noted previously, this can be done by capillary wetting, direct pressurization, electrophoresis or any other method that can impel the colloids in the code fluid into the microfluidic chip. The user sets the reader operation entering input parameters. The reader determines if there is a secure encrypted wireless communication with the authentication entity.

A loading interface 704 accepts code fluid 702 and positions it in a fluidic channel for injection into microfluidic chip 705. Fluidic chip 705 then reads the lateral displacement and mapping information and then stores it in controller 709. The results are then checked out with the authentication entity to confirm the results. Microfluidic chip 705 contains the nano-DLD and/or mapping devices which will decipher the constituents of code fluid 702.

Nano-DLD requires a pressure driven flow, while the DNA mapping requires electrophoresis. To drive these two flows, driving mechanism 707 locks onto microfluidic chip 705 and positions the necessary pump valves and electrodes onto the chip for driving pressure and electrophoresis flows, respectively. Once loaded and driven into the microfluidic chip under steady state, the encoding can be read out by scanning the read-out regions of the nano-DLD and mapping devices on detector 706.

Detector 706 generally consists of a light source and detector element (e.g. photodiode or CCD camera). Laser induced fluorescence or scattering is a preferred method for imaging the colloids in the devices, and multiple detection modalities can be used in the detector to read out the code fluid.

The interplay of detector 706 and driving mechanism 707 is orchestrated by controller 709 (e.g. microcontroller or micro-computer) which regulates power supply 708 to the machine and handles the input/output at user interface 710. The user interface can consist of a button grid, touch-screen, computer terminal, etc., which allows the party running the authentication process to set-up and monitor the deciphering process.

The detector's digital output of the code fluid is sent to controller 709, which curates it and transmits it using transceiver 711 microfluidic chip 705 (or other mechanism) for analysis and verification. Verification takes place remotely, via a dedicated server (not shown).

The dedicated server compares the submitted information (including the product to be authenticated, any time stamp data that is of importance to the authenticator, and the transmitted read out of the code fluid) to the stored "master copy" which was generated by the code manufacture at the time of formulation. A positive match results in a verified message being transmitted back to the reader; a false match results in an error message. The reader is encased in a housing to protect its electronics and sensors, as indicated by box outline within 703.

Figure 8:
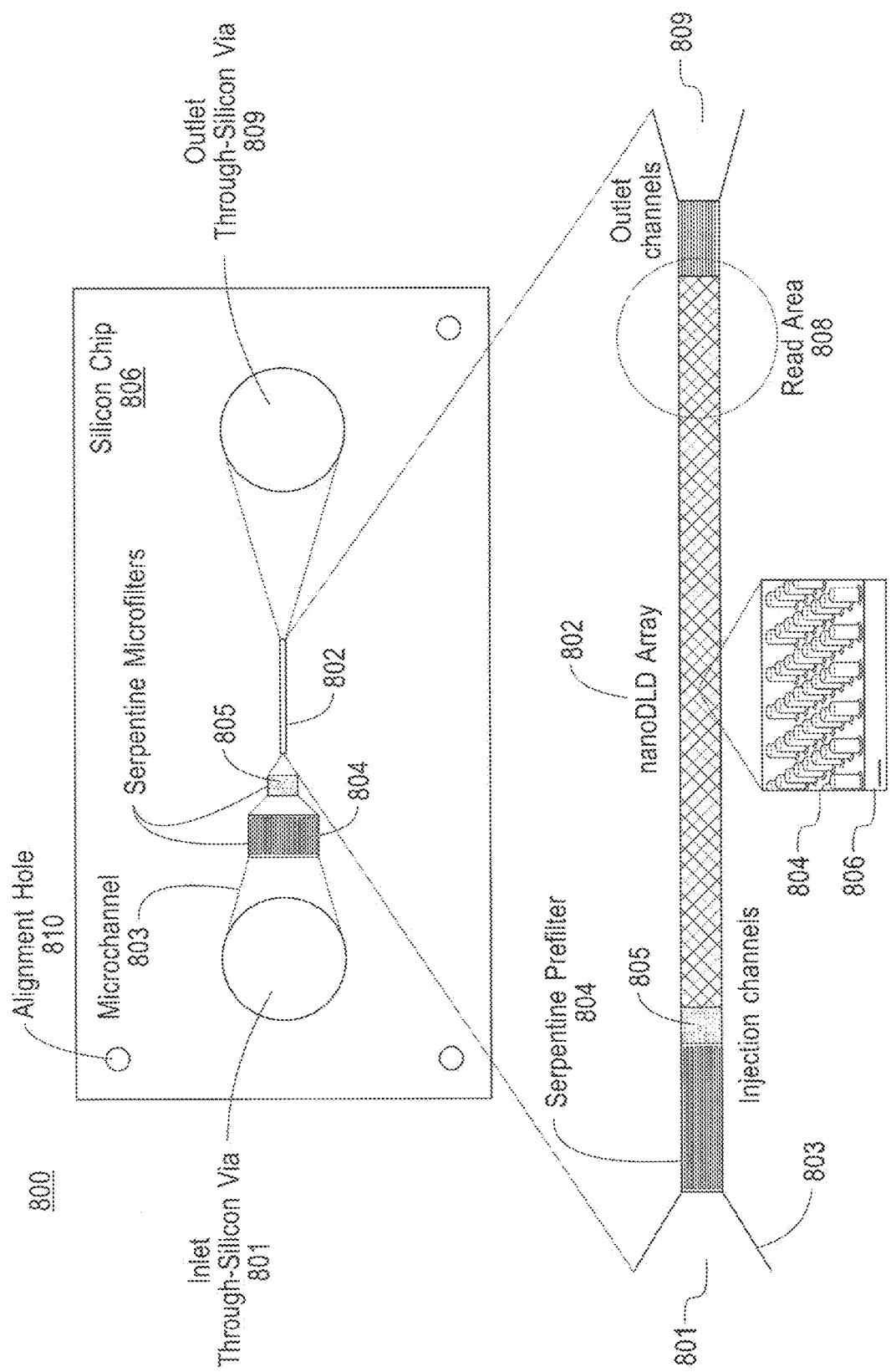
FIG. 8 is a schematic representation of nanoscale deterministic lateral displacement (nano-DLD) device for reading colloidal solutions.

FIG. 8 at 800 illustrates a top view schematic representation of a nanoscale deterministic lateral displacement (nano-DLD) device for reading colloidal solutions.

The device is fabricated onto a silicon substrate 806 using standard nanolithography techniques known in the art. Nano-DLD array 802 consists of an inlet through silicon via 801 extending to microchannel 803 into which has been etched a periodic lattice of pillars 804 (or other prismatic features) with an angle (glide transition, tilt, etc.) that directs the pillar lattice vector at an angle to the channel.

A set of serpentine filters 804, 805 are staged stream of nano-DLD array 802 to capture any large particulates that could potentially clog the array (e.g. microbes, debris, etc.).

Inlet 801 and outlet 809 of the array plumb to through-silicon vias (through-holes not shown) in the substrate. The vias allow liquid to be injected into/out of the array and facilitate wetting and priming of the device prior to use.

Read area 808 on the device is at the end of nano-DLD array 802, where maximum lateral separation has occurred. This location is imaged for read-out of the formulation code. A set of small through-holes, e.g., alignment hole(s) 810, are set asymmetric into silicon chip 806 to allow proper alignment and securing of the chip into the reader.

Figure 9:
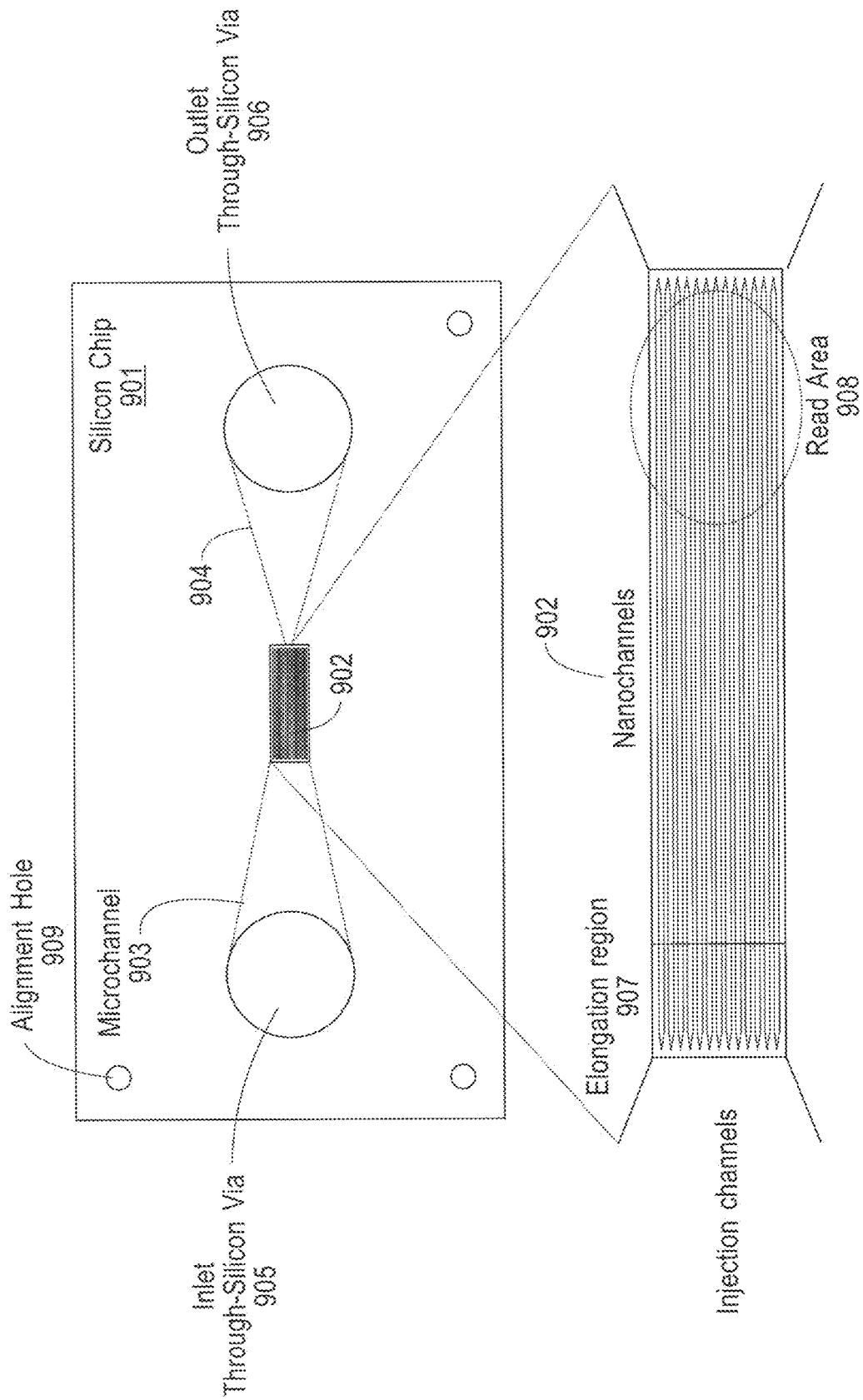
FIG. 9 is a schematic representation of DNA mapping for reading DNA strand codes in the formulation.

FIG. 9 at 900 illustrates a top view of a schematic representation of a DNA mapping device for reading DNA strand codes in the formulation.

The device is fabricated onto a silicon substrate 901 using standard nanolithography techniques known in the art. Mapping device 900 consists of a series of parallel nanochannels 902 which bridge two microchannel reservoirs where DNA is introduced at injection channel 910. Microchannels at inlet 903 and outlet 904 of the array plumb to through-silicon vias 905, 906 (through-holes) in silicon chip substrate 901.

Vias 905 and 906 allow liquid to be injected into/out of the array and facilitate wetting and priming of the device prior to use. The entrance to the nanochannels is fabricated with an elongation region 907, which can use any number of standard, known structural features to uncoil and stretch out DNA prior to its loading into the nanochannel. This is a prerequisite for mapping the DNA. Read area 908 can be located at almost any location along the nanochannel 902 route, save for the entrance (depicted at the outlet 906). A set of small through-holes, (e.g., alignment hole 909), are set asymmetric into silicon chip 901 to allow proper alignment and securing of the chip into the reader 908.

Figure 10:
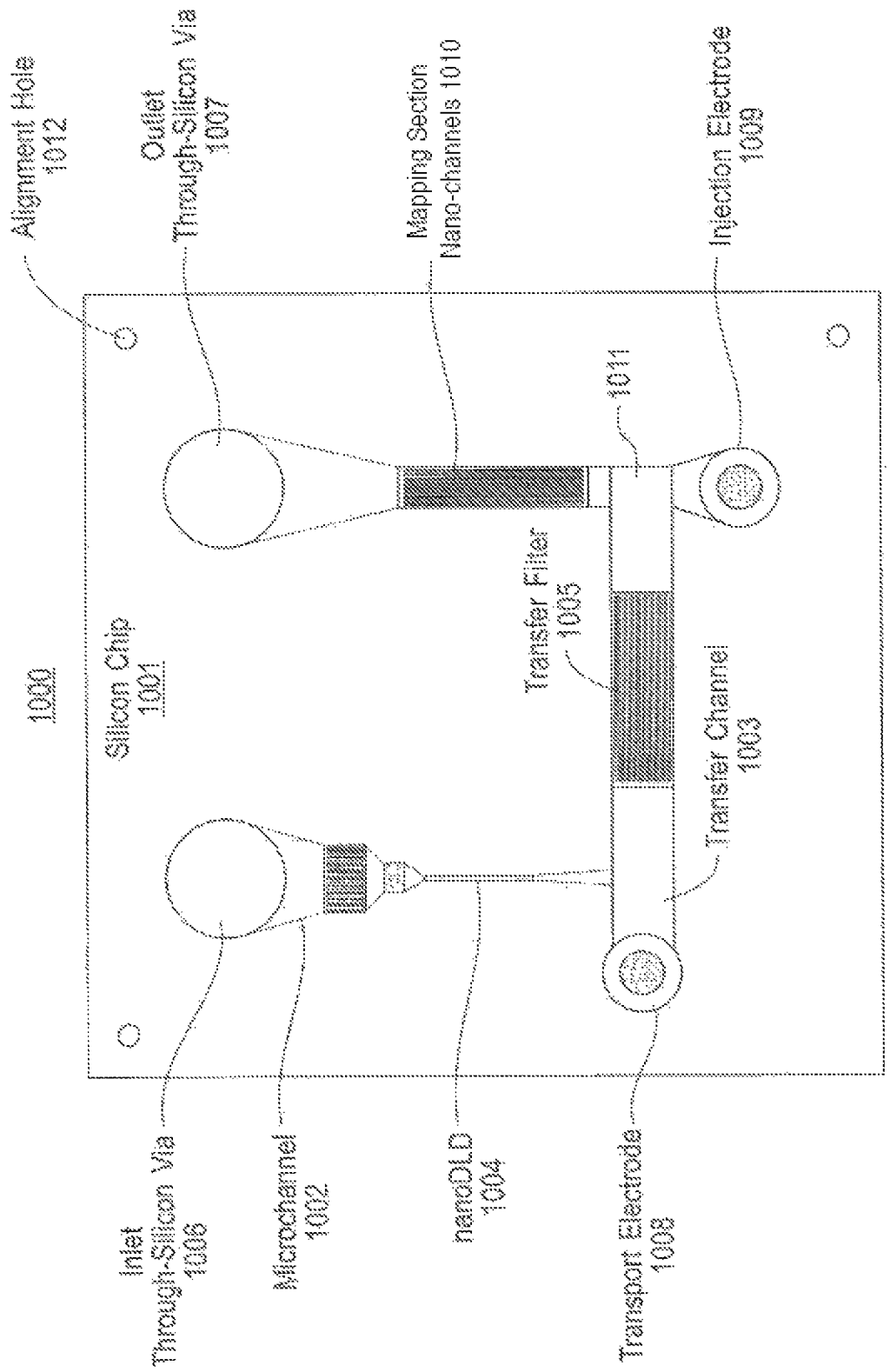
FIG. 10 is a schematic representation of nanoscale deterministic lateral displacement (nano-DLD) device for reading colloidal solutions.

FIG. 10 at 1000, illustrates a top view of a schematic representation of a device 1000 combining nano-DLD 1004 and DNA mapping in sequence to allow more complicated colloidal formulation reading.

Device 1000 is fabricated onto a silicon substrate 1001 using standard nanolithography techniques. The nano-DLD 1004 and mapping sections 1011 are the same as depicted in FIGS. 8 and 9.

The nano-DLD read-out must be performed first, as the colloids can interfere/clog the nanochannels in mapping section 1010. A microchannel 1002 and a transfer channel 1003 link the output of the nano-DLD to the input 1011 of mapping section 1010.

A filter region 1005 is included in transfer channel 1003 to impede all colloids, of any size/shape, that would clog the nanochannels downstream. Two through-silicon vias 1006 and 1007 with electrodes 1008 and 1009 respectively in their bore are placed at the beginning and end of transfer channel

1003. The first electrode, transport electrode 1008, is used to electrophoretically drive DNA across transfer channel 1003 to the area outside the mapping section. This is because the nano-DLD section uses a pressure drive to operate, but the pressure drop is significant across the nano-DLD array and cannot be used to drive DNA through the mapping nanochannels. Transport electrode 1008 can provide the force to move DNA into position for mapping. The second electrode, e.g., injection electrode 1009, is used to drive the DNA into the nanochannel and move it for reading.

The counter electrode 1009 for the injection process is located in the bore of the outlet through-silicon via. In operation, a potential is applied between the transport electrode 1008 and injection electrode 1009 to drive DNA into position by the mapping channels 1010, and then a potential is applied across the injection electrode 1009 and outlet through-silicon via 1007 to drive DNA into nanochannel 1010 for reading. A set of small through-holes, e.g., alignment holes 1012, are set asymmetric into silicon chip 1001 to allow proper alignment and securing of chip 1001 into the reader.

Figure 11:
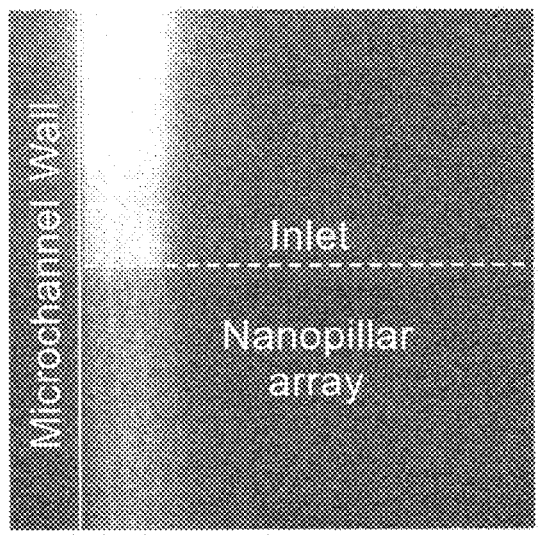
FIGS. 11-13 depict a sequential example of an embodiment of a formulation code being read out by a nano-DLD array.
Figure 12:
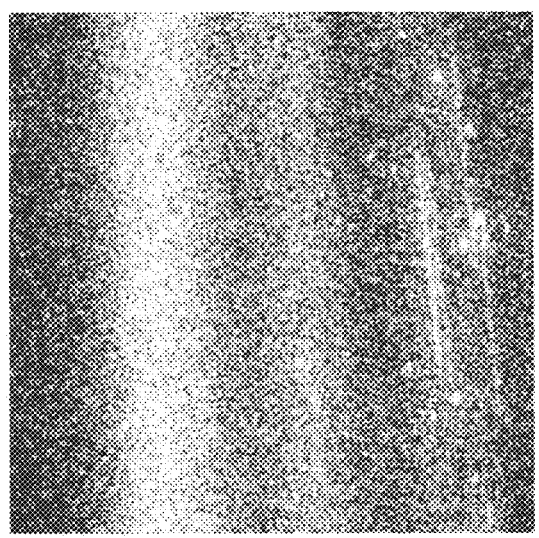
Figure 13:
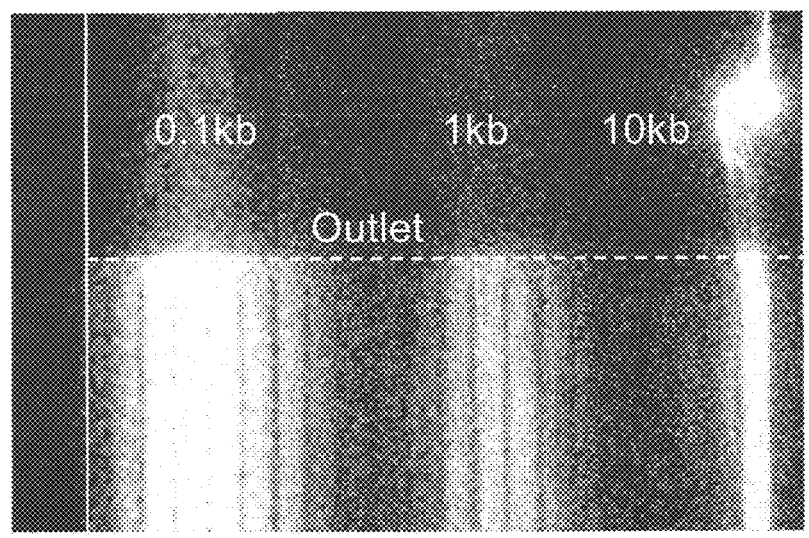

FIGS. 11-13 depict an example of an embodiment of a formulation code being read out by a nano-DLD array. FIGS. 11-13 illustrate the results of fluorescent images at 470 nm excitation and 510 nm emission, of a mixture of YOYO-1 labeled dsDNA fragments (0.1, 1.0 and 10.0 kb) being injected into a 200 nm gap nano-DLD array.

In FIG. 11, at an inlet, the DNA formulation is injected as a stream on the left-hand wall of a microchannel. In FIG. 12, stream processing through the array causes the different fragment populations to deflect at different angles, resolving, as shown in FIG. 13 into three individual peaks with different peak intensities at the outlet of the nano-DLD array.

Figure 14:
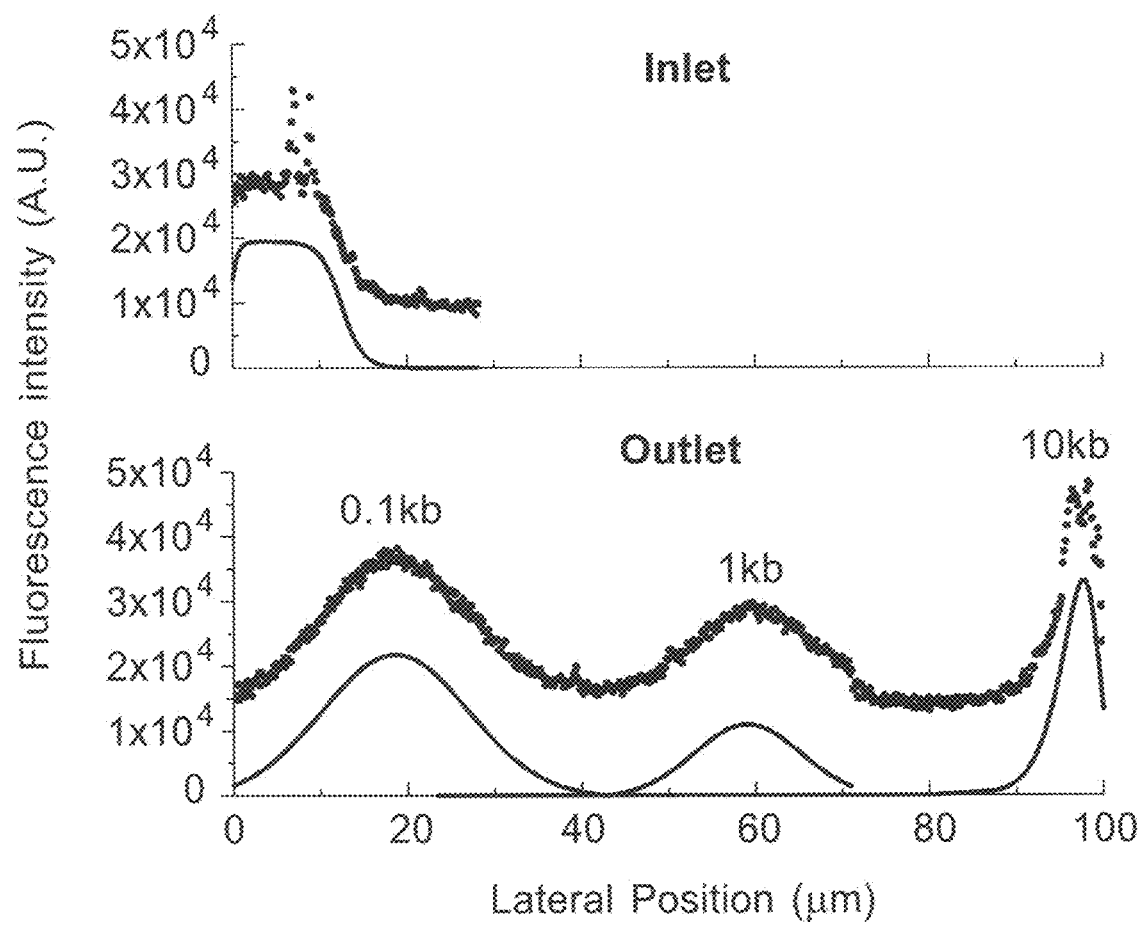
FIG. 14 is a graph plotting fluorescence intensity (A.U.) as a function of lateral position ($\mu$m) wherein the pattern of peaks is the code from the formulation used.

FIG. 14 is a graph plotting fluorescence intensity (A.U.) as a function of lateral position (tam) wherein the fluorescence line profiles at the inlet and outlet, show the resolution of the formulation into three distinct peaks. The pattern of peaks is the code from this formulation.

As shown in FIGS. 6 and 7, the present invention contemplates implementation on a system or systems that provide multi-processor, multi-tasking, multi-process, and/or multi-thread computing, as well as implementation on systems that provide only single processor, single thread computing.

Multi-processor computing involves performing computing using more than one processor. Multi-tasking computing involves performing computing using more than one operating system task.

A task is an operating system concept that refers to the combination of a program being executed and bookkeeping information used by the operating system. Whenever a program is executed, the operating system creates a new task for it.

The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system).

Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium as mentioned above, can be a tangible device that can retain and store instructions for use by an instruction execution device. The computer readable storage medium may be, for example, but is not limited to electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing.

A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers.

A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein and at FIGS. 4 and 5, with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The aforementioned computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the FIGS. 6 and 7 illustrate the architecture functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the FIGS. 6 and 7.

For example, two blocks shown in succession may, in fact, be executed substantially concurrently, or the blocks may sometimes be executed in the reverse order, depending upon the functionality involved.

It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What we claim and desire to protect by Letters Patent is:

1. A composition of matter for authenticating a product's origin, properties and intended transaction history that reduces counterfeiting by providing a high barrier to copying a traveling authentication code, said composition of matter comprising:
    a solvent; and
    diverse hard-bodied colloidal particles that are suspended in the solvent and have a variety of physical shapes, sizes, and constructs;
    wherein volume fractions of different types of the diverse hard-bodied colloidal particles compose at least a portion of the traveling authentication code;
    wherein the diverse hard-bodied colloidal particles consist essentially of components selected from a list consisting of: metal and metal oxide particles, semiconductor quantum dot particles, organic layer stabilized metal core nanoparticles, and polymer particles and microbeads;
    wherein essentially all of the diverse hard-bodied colloidal particles are of spherical, prismatic, and polyhedral shapes.

2. The composition of matter defined in claim 1 wherein said diverse hard-bodied colloidal particles in said solvent constitute a physical code.

3. The composition of matter defined in claim 2 wherein said physical code incorporates said diverse hard-bodied colloidal particles having different colloidal properties in set ratios.

4. The composition of matter defined in claim 3 wherein said physical code has a code value consisting of the volume fraction of each shape of said diverse hard-bodied colloids.

5. The composition of matter according to claim 2, wherein the diverse hard-bodied colloidal particles have diameters between about 1 nm and about 100 .mu.m.

6. The composition of matter according to claim 5, wherein the diverse hard-bodied colloidal particles have diameters of 10-1000 nm.

7. The composition of matter according to claim 1, further comprising:
    nucleotide-based polymeric particles synthesized and encoded with specific base sequences;
    wherein the nucleotide-based polymeric particles are selected from a group consisting of: deoxyribonucleic acid (DNA), ribonucleic acid (RNA), peptide nucleic acid (PNA), and a member of a family of double-helical DNA-like polymers;
    wherein one of four normal bases in the nucleotide-based polymer particles is replaced with a cationic, anionic, or neutral analog.

8. The composition of matter according to claim 7, wherein at least one of the specific base sequences is a partial DNA chain that includes markers attached to the partial DNA chain at selected sites;

wherein the markers comprise fluorescently labeled cDNA fragments.

9. The composition of matter according to claim 8, wherein a sequence of the markers along the partial DNA chain composes at least another portion of the traveling authentication code.

10. The composition of matter according to claim 1, wherein the solvent comprises:
- an emulsifier;
- an anti-coagulant;
- a blocker against non-specific adsorption;
- an anti-photo-bleaching agent;
- a stabilizer;
- at least one of an antibiotic, a salt, a pH buffer, and a sensitizer; and
- at least one of anti-foaming, thickening, and thinning agents.

11. A composition of matter for authenticating a product's origin, properties and intended transaction history that reduces counterfeiting by providing a high barrier to copying a traveling authentication code, said composition of matter comprising:
- a solvent; and
- nucleotide-based polymeric particles synthesized and encoded with specific base sequences;
- wherein the nucleotide-based polymeric particles are selected from a group consisting of: deoxyribonucleic acid (DNA), ribonucleic acid (RNA), peptide nucleic acid (PNA), and a member of a family of double-helical DNA-like polymers;
- wherein one of four normal bases in the nucleotide-based polymer particles is replaced with a cationic, anionic, or neutral analog;
- wherein at least one of the specific base sequences is a partial DNA chain that includes markers attached to the partial DNA chain at selected sites;
- wherein the markers comprise fluorescently labeled cDNA fragments;
- wherein a sequence of the markers along the partial DNA chain composes at least a portion of the traveling authentication code.

12. The composition of matter according to claim 11, further comprising:
- diverse hard-bodied colloidal particles that are suspended in the solvent and have a variety of physical shapes, sizes, and constructs;
- wherein volume fractions of different types of the diverse hard-bodied colloidal particles compose at least another portion of the traveling authentication code.

13. The composition of matter according to claim 12, wherein the diverse hard-bodied colloidal particles consist essentially of components selected from a list consisting of: metal and metal oxide particles, semiconductor quantum dot particles, organic layer stabilized metal core nanoparticles, and polymer particles and microbeads.

14. The composition of matter according to claim 13, wherein essentially all of the diverse hard-bodied colloidal particles are of spherical, prismatic, and polyhedral shapes.

15. The composition of matter according to claim 11, wherein the solvent comprises:
- an emulsifier;
- an anti-coagulant;
- a blocker against non-specific adsorption;
- an anti-photo-bleaching agent;
- a stabilizer;
- at least one of an antibiotic, a salt, a pH buffer, and a sensitizer; and
- at least one of anti-foaming, thickening, and thinning agents.

* * * * *